US012589034B2

(12) United States Patent
Weimer et al.

(10) Patent No.: US 12,589,034 B2
(45) Date of Patent: Mar. 31, 2026

(54) METHOD FOR CARRYING OUT A SYSTEM TEST OF A LASER PROCESSING SYSTEM, CONTROL UNIT AND LASER PROCESSING SYSTEM

(71) Applicant: Carl Zeiss Meditec AG, Jena (DE)

(72) Inventors: Wolf Weimer, Jena (DE); Gregor Stobrawa, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 132 days.

(21) Appl. No.: 18/552,216

(22) PCT Filed: Mar. 11, 2022

(86) PCT No.: PCT/EP2022/056281

§ 371 (c)(1),
(2) Date: Sep. 25, 2023

(87) PCT Pub. No.: WO2022/200072

PCT Pub. Date: Sep. 29, 2022

(65) Prior Publication Data

US 2024/0180747 A1 Jun. 6, 2024

(30) Foreign Application Priority Data

Mar. 25, 2021 (DE) ..................... 10 2021 202 947.7

(51) Int. Cl.
| *A61B 17/00* | (2006.01) |
| *A61F 9/009* | (2006.01) |
| *G01M 11/08* | (2006.01) |

(52) U.S. Cl.
CPC ............. *A61F 9/009* (2013.01); *G01M 11/08* (2013.01); *A61B 2017/00154* (2013.01); *A61B 2017/00725* (2013.01)

(58) Field of Classification Search
CPC ............ A61F 9/009; A61F 2009/00855; A61F 2009/00872; A61F 2009/00897;
(Continued)

(56) References Cited

U.S. PATENT DOCUMENTS 8,430,869 B2 4/2013 Wölfel et al.
9,138,349 B2 9/2015 Wölfel et al.
(Continued)

FOREIGN PATENT DOCUMENTS

DE 102011101638 A1 1/2012
DE 102013008645 B3 8/2014
(Continued)

OTHER PUBLICATIONS

Search Report by the German Patent and Trademark Office issued in DE 10 2021 202 947.7, to which this application claims priority, mailed Feb. 11, 2022, and English-language translation thereof.
(Continued)

*Primary Examiner* — Michelle M Iacoletti
*Assistant Examiner* — Judy Dao Tran
(74) *Attorney, Agent, or Firm* — Pearl Cohen Patentanwälte PartGmbB; Michael McCandlish

(57) ABSTRACT

A method for carrying out a system test of a laser processing system is disclosed. The method includes the execution of a functional test of a control element of the laser processing system. The method further includes the determination of a variable parameter and the determination of an influence of the determined variable parameter on an intended execution of a laser processing by means of the laser processing system. The execution of the functional test of the control element and the determination of the variable parameter overlap at least partially in time.

18 Claims, 2 Drawing Sheets

(58) Field of Classification Search
CPC ................ A61F 9/00827; G01M 11/08; A61B
2017/00154; A61B 2017/00725
See application file for complete search history.

(56)                          References Cited

U.S. PATENT DOCUMENTS

| | | | |
|---|---|---|---|
| 2002/0193704 A1 | 12/2002 | Goldstein et al. | |
| 2007/0010803 A1* | 1/2007 | Bischoff | A61F 9/00825 |
| | | | 606/4 |
| 2007/0173792 A1 | 7/2007 | Arnoldussen | |
| 2007/0225692 A1* | 9/2007 | Somani | G01J 1/4257 |
| | | | 250/252.1 |
| 2008/0078752 A1 | 4/2008 | Bischoff et al. | |
| 2008/0165320 A1* | 7/2008 | Heiberger | A61B 3/103 |
| | | | 606/4 |
| 2010/0106143 A1* | 4/2010 | Riedel | A61F 9/00804 |
| | | | 606/5 |
| 2011/0034911 A1* | 2/2011 | Bischoff | A61F 9/009 |
| | | | 606/4 |
| 2011/0264081 A1 | 10/2011 | Reich et al. | |
| 2011/0276042 A1* | 11/2011 | Dick | A61F 9/00814 |
| | | | 606/5 |
| 2012/0172853 A1* | 7/2012 | Riedel | A61F 9/009 |
| | | | 606/4 |
| 2014/0347655 A1 | 11/2014 | Jurca | |
| 2016/0296375 A1* | 10/2016 | Reich | A61F 9/00825 |
| 2020/0260954 A1* | 8/2020 | Gonzalez | A61B 3/102 |
| 2020/0289317 A1* | 9/2020 | Bareket | A61F 9/008 |

FOREIGN PATENT DOCUMENTS

| | | |
|---|---|---|
| DE | 102013226961 B4 | 2/2019 |
| EP | 2648666 A1 | 6/2012 |
| GB | 2480525 A | 11/2011 |
| WO | 2008040436 A1 | 4/2008 |
| WO | 2009146906 A2 | 12/2009 |
| WO | 2012076031 A1 | 6/2012 |

OTHER PUBLICATIONS

International Preliminary Report on Patentability issued in PCT/EP2022/056281, to which this application claims priority, mailed Oct. 5, 2023.
International Search Report and Written Opinion issued in PCT/EP2022/056281, to which this application claims priority, mailed Jun. 28, 2022 (English language translation enclosed).
Intention to grant European patent application EP 22 713 931.8 dated Nov. 5, 2025, and English-language machine translation thereof.

* cited by examiner

METHOD FOR CARRYING OUT A SYSTEM TEST OF A LASER PROCESSING SYSTEM, CONTROL UNIT AND LASER PROCESSING SYSTEM

CROSS REFERENCE TO RELATED APPLICATIONS

This application is a national stage application of international patent application PCT/EP2022/056281, filed Mar. 11, 2022, designating the U.S. and claiming priority from German patent application DE 10 2021 202 947.7, filed Mar. 25, 2021 and the entire content of both applications is incorporated herein by reference.

TECHNICAL FIELD

The present disclosure relates to a method for carrying out a system test of a laser processing system, a control unit and a laser processing system. Consequently, the disclosure is in the field of laser processing systems, and in particular in the field of ophthalmological laser processing systems for eye surgery.

BACKGROUND

Ophthalmological laser processing systems are therapy systems for eye surgery. Their flawless function is a prerequisite for the success of therapy and for the safety of the patient and user. This often requires automatic or semiautomatic checking of specific properties of the laser processing systems before a treatment.

The flawless function may also include a requirement to achieve a specific accuracy during therapy. For this purpose, targeted measures for improving accuracy may be carried out. This may be the case in particular if changes to the laser processing system necessitate a calibration. Such changes may be caused by external influences, for example. Such changes may occur if a laser processing system is combined with other medical devices or itself includes a combinable accessory. In this regard, for example, the use of a patient interface in the form of a sterile consumable may produce variability in the system which necessitates a calibration to compensate for this variability.

Often, therefore, before a treatment of an eye by means of the laser processing system, one or more test methods and/or system tests, which may comprise tests and/or calibrations, are employed in order to ensure that the laser processing system fulfils its function safely and effectively. In this case, the individual tests and/or calibrations which a system test comprises are carried out sequentially one after another.

A system test may comprise a calibration for example if the use of the laser processing system includes the use of exchangeable contact glasses, which may possibly vary on account of manufacturing tolerances in terms of their thickness, their diameter, their decentration (lateral offset relative to the optical axis), their shape (radius of curvature) and/or with regard to other properties. For the improvement of the achievable precision of the laser processing system and a treatment to be carried out therewith, the ascertained parameters or the results of a system test can be used for optimizing the control signals for the scanning device.

There are various possibilities for temporally arranging a system test or the individual tests and/or calibrations of a system test, for example immediately after switching on the laser processing system and/or directly before therapy. It is advantageous to carry out all tests and/or calibrations of the system test directly before the use of the laser processing system for treating an eye, in order to minimize that time period between the respective tests and/or calibrations and the treatment in which undesired changes may occur. Such undesired changes may be caused for instance by thermal drifts, spontaneous component faults, mechanical changes or alterations of settings as a result of inadvertent touching and/or contamination of the contact glass and/or of other components. However, carrying out all tests and/or calibrations of the system test directly before carrying out treatment conventionally requires the patient to be in a treatment-ready state throughout the duration for carrying out the system test. This may require the patient to be in an undesired constrained position during the entire time period of the system test and in the course of this the patient may need to wear surgery clothing and/or an eyelid holder, may need to be medicated and/or may need to stay docked to the laser processing device, in particular to the contact glass. If the system test has a considerable time duration, this may have a disadvantageous effect on the patient's well-being or even cause stress.

It is an object of the disclosure to reduce the required time duration for a system test of a laser processing system.

This object is achieved by means of a method for carrying out a system test of a laser processing system, a control unit and a laser processing system discussed in the following description.

In a first aspect, the disclosure relates to a method for carrying out a system test of a laser processing system. In this case, the method comprises carrying out a functional test of a control element of the laser processing system. The method additionally comprises ascertaining a variable parameter and determining an influence of the ascertained variable parameter on intended carrying out of laser processing by means of the laser processing system. In this case, carrying out the functional test of the control element and ascertaining the variable parameter overlap one another at least partly in time.

In a further aspect, the disclosure relates to a control unit for a laser processing system, wherein the control unit is configured, in the context of a system test of the laser processing system, to carry out a functional test of the control element of the laser processing system. Moreover, the control unit is configured to ascertain a variable parameter and to ascertain an influence of the variable parameter on intended carrying out of laser processing by means of the laser processing system. Furthermore, the control unit is configured to carry out the functional test of the control element and the ascertaining of the variable parameter in a manner overlapping one another at least partly in time and to receive and/or to evaluate resultant measurement data and/or measurement results at least partly simultaneously.

In a further aspect, the disclosure relates to a laser processing system comprising a control unit according to the disclosure.

In this case, a system test is a method for checking and/or ensuring the functionality of the laser processing system. In this case, the system test can comprise one or more tests and/or one or more calibrations. A system test can be implementable in a continuous period of time or in a plurality of periods of time separated from one another. A system test is optionally configured in such a way that it is implementable in an automated manner, in particular by the laser processing system itself. However, in accordance with some exemplary embodiments, system tests which are implementable with the aid of an operator are also possible.

In this case, a test constitutes a functional test of a control element by means of at least one sensor. A calibration constitutes a measurement of one or more properties of a variable element and/or of a variable component using at least one sensor and the derivation of an adaptation of future control signals in accordance with the measurement values ascertained.

In this case, a laser processing system is a system which enables the processing of an object by means of laser radiation. In particular, a laser processing system can be designed as an ophthalmic laser processing system and can serve for the surgical processing or treatment of a human and/or animal eye of a patient. Optionally, the laser processing system can be designed as an apparatus for correcting myopia or hyperopia and/or astigmatism of an eye. Optionally, a laser processing system can comprise a laser source and/or receive a laser beam from an external, separate laser source. The laser source may comprise a femtosecond laser and/or a picosecond laser, or is designed as such. In accordance with other exemplary embodiments, however, the laser source can also comprise an excimer laser. The laser beam can be provided as a pulsed laser beam, or else as a continuous wave laser beam (cw).

In this case, a control element is an element which is controllable by open-loop and/or closed-loop control. By way of example, the control element can constitute an actuator. Optionally, the control element can be designed as or comprise a controllable optical element, such as, for instance, as an adaptive mirror and/or as one or more movable mirrors. In particular, a control element can be designed to control the laser beam of the laser processing system, for instance by way of targeted deflection of the laser beam. By way of example, the control element can be designed as a laser beam scanner, i.e. as a scanning device, by means of which the laser beam can be adapted in terms of its position and/or direction of propagation by way of one or more movable mirrors.

Ascertaining a variable parameter constitutes obtaining information about the actual value and/or state of the variable parameter at least at the point in time of ascertainment. In this case, the ascertained information regarding the variable parameter is representative of the variable portion of the variable parameter. By way of example, that can involve information about the actual configuration of elements and/or components which are subjected to changes. Alternatively or additionally, that can involve other variables that do not represent a property of the laser processing system, such as, for instance, the position and/or orientation of an eye to be treated.

The fact that carrying out the functional test of the control element and ascertaining the variable parameter overlap at least partly in time means that they are carried out not fully separately from one another in time. In other words, this means that at at least one point in time, both carrying out the functional test of the control element and ascertaining the variable parameter take place. Optionally, both processes can also completely overlap, that is to say that both begin at the same point in time and/or end at the same point in time, or carrying out the functional test of the control element or ascertaining the variable parameter then begins and ends while the respective other process is still ongoing.

The fact that the measurement data and/or measurement results can be received and/or evaluated by the control unit at least partly simultaneously means in this case that the computing unit need not conclude the reception and/or evaluation of the first measurement data and/or measurement results before second measurement data and/or measurement results can be received and/or evaluated. In other words, a plurality of measurement data and/or measurement results can be received and/or processed by the control unit at least partly in parallel. This may impose corresponding hardware requirements on the control unit, in particular with regard to the processor power and/or the main memory, in order to enable a plurality of signals and/or data to be received and/or evaluated in parallel.

According to the disclosure, at least the functional test of the control element and ascertaining the variable parameter and determining the influence on the intended carrying out of the laser processing may be carried out at least partly simultaneously, and the time duration required for the system test may be reduced. In other words, a test and a calibration in the context of the system test are carried out at least partly simultaneously. Consequently, a larger proportion or even all of the tests and/or calibrations of the system test can be carried out directly before the use of the laser system, without in this case exceeding a time measure that is acceptable to the patient and/or user.

Moreover, a division of tests and/or calibrations which are carried out directly before processing or treatment by means of the laser processing system, and other tests and/or calibrations which are carried out at a different point in time, may not absolutely be necessary in order that that duration of the system test directly before the processing or treatment during which a patient has already been docked, for instance, is limited to an acceptable measure.

Furthermore, the waiting time during which the patient to be treated may need to stay in the docked state before the beginning of treatment can be reduced and the unpleasantness for the patient as a result of the waiting can accordingly be reduced. In addition, it is possible, if appropriate, to reduce a dose of the medication for the patient that is required for carrying out the treatment, since the time interval between administering the medicaments and the beginning of treatment can be shortened.

Optionally, the control element is designed as a scanning device for beam deflection. The control element can be designed as a laser beam scanner (also referred to as a scanning device), as an actuator, as an acousto-optic modulator (AOM), as an electro-optic modulator and/or as an adaptive mirror or can comprise at least one of these elements. In this case, optionally the functional test of the control element comprises or consists of a test of the scanning device by means of at least one control element sensor. A negative result of the test or of the functional test may then indicate a fault, where the control element and/or the sensor may be the cause of the fault. In order to increase the reliability of the detection of a fault of the control element, optionally two or more redundant sensors can be used for the functional check of the control element. Therefore, the correct functioning of the scanning device for beam deflection can be reliably checked before the beginning of the treatment.

Optionally, the test comprises controlling the scanning device in such a way that the scanning device is set in accordance with a scanning pattern for guiding a laser beam along a predetermined scanning path, wherein a setting of the scanning device for respectively deflecting the laser beam by way of the scanning device is ascertainable by means of the at least one control element sensor. Within the meaning of the disclosure described here, a scanning pattern is a sequence of control data which can be fed to the scanning device in order to bring about a sequence of beam guiding configurations. By contrast, the scanning path is a sequence of virtual focus positions which results from the sequence of the associated beam guiding configurations, i.e. from the scanning pattern. In other words, the scanning pattern is a sequence of settings for the scanning device which has the effect that the focus is movable along the scanning path. In this case, a virtual focus, which may also be referred to as a virtual focus position, is a theoretical position of a laser focus to which a specific configuration of the beam guiding and in particular of the scanning device can be assigned. In this case, the set of virtual focus positions can be larger than the set of real focus positions since not every configuration of the scanning device must necessarily lead to a real focus. In this case, a real focus, which may also be referred to as a real focus position, is a position of a laser focus which arises as a result of laser radiation which passes through a specific configured beam guiding (optical unit) and in particular a specifically configured scanning device. A variable configuration of the beam guiding can serve to make it possible to attain each real focus position with at least one specific configuration of the scanning device.

In this case, the guiding of the laser beam means that the laser beam is deflected by means of the scanning device in such a way that the virtual and/or real focus is guided along the predefined scanning path. In this case, it is unimportant whether, in the setting of the scanning device, a laser beam is actually incident and deflected by the scanning device, i.e. whether a real focus arises, or whether the settings of the scanning device are effected without a laser beam being incident and accordingly only a virtual focus is deflected. In other words, the settings and the checking of the scanning device can also be performed in such a way that no laser beam is actually deflected by the scanning device in this case, rather only the suitability of the scanning device for the desired deflection of the laser beam is checked. This can be done for example by means of suitable sensors at the scanning device. In other words, the guiding of the laser beam along a predetermined scanning pattern corresponds to the controlled bringing about of a scanning path, i.e., a positional change of the possibly focused laser beam in the plane or the volume in which the laser beam impinges on the object to be processed. Accordingly, two different types of functional tests can be used for the scanning device. A first type involves merely a test of the configuration of the beam guiding, i.e. of the mechanical mirror positions and of the associated virtual focus positions. A second type involves a test of the real focus positions, for example by way of optical detection and evaluation of a confocal back-reflection of the respective real focus.

Optionally, the laser beam can also be guided in a direction parallel to the optical axis, for instance by the alteration of the position of the focus along the beam direction, for example by way of a change in the convergence angle of the laser beam and/or the position of the focusing element. As a result, the laser beam or focus can be guided along a three-dimensional scanning path. In this case, the caused scanning path of the scanning pattern can be designed to be continuous, or can have interruptions. Moreover, the scanning path can have a plurality of segments and/or can have a plurality of points onto which the laser beam is applied and optionally focused along a predetermined scanning path, i.e. in a predetermined order. In other words, the scanning pattern of the test is optionally designed in such a way that the associated scanning path comprises all focus positions or laser beam positions provided for predetermined laser processing by the laser processing system. Optionally, the predetermined scanning pattern can be chosen in such a way that the scanning pattern is representative of the entire usable range of values of the scanning device. This affords the advantage that the test is universally usable and does not have to be created individually just for individual planned treatments. Moreover, a scanning pattern can optionally be chosen in such a way that the required test duration is shorter than a possible intended treatment. The testing of the scanning device may make it is possible to check the functionality of the scanning device for deflecting the laser beam along the path predetermined for the planned treatment. The focusing of the laser beam is optional in this case. Accordingly, there may be applications in which the laser beam is focused, and other applications in which the laser beam is not focused. If focusing is effected, the at least one focusing element can be arranged upstream of the scanning device in accordance with some exemplary embodiments, and can be arranged downstream of the scanning device in accordance with other exemplary embodiments. Optionally, with the use of femtosecond lasers, the laser beam is focused only downstream of the scanning device, i.e. after deflection. Optionally, with the use of excimer lasers, the laser beam is focused upstream of the scanning device and the convergent laser beam is then deflected.

Optionally, the scanning pattern is designed in such a way that the laser beam in the region of the scanning path associated with the scanning pattern at least partly detects a reference object characterizing the variable parameter, and the variable parameter is ascertainable on the basis of a signal resulting therefrom. Thus, the detection of the reference object characterizing the variable parameter can be combined with the test of the control element and can accordingly be concomitantly processed during the course of the functional check or the test. This is possible for such reference objects which are situated in a region accessible to the laser beam, i.e. lie in the region which can be detected by means of the laser beam deflected by the scanning device.

Optionally, the signal resulting from the detection of the reference object by the laser beam comprises a reflected portion of the laser beam and/or a scattered portion of the laser beam and/or an emission signal excited by the laser beam. In this case, the signal is detectable by a reference object sensor. In this regard, for instance, the reference object can reflect and/or scatter a part of the incident laser beam, such that the reflected and/or scattered portion is detectable by means of the reference object sensor. This can serve for instance for testing the location of the real focus position in relation to a reference object. By way of example, this can be done by means of interface detection, as described for instance in WO 2008/040436 A1.

Optionally, the laser beam is emitted only at such locations of the predetermined scanning path or with such configurations of the scanning pattern through the laser processing system at which the laser beam at least partly detects the reference object. That is not at odds with the fact that optionally the laser source of the laser processing system emits laser radiation even if the laser processing system does not emit a laser beam, since the laser beam can be blocked and/or diverted within the laser processing system, for example, and consequently is emitted by the laser source but is not applied by the laser processing system to a patient or an object to be processed. Thus, the test or the functional check can be carried out even if the patient has already been docked to the laser processing system or an object to be processed has already been docked to the laser processing system, in particular by means of a test of the virtual focus position(s). In this case, the functional check of the control element can be effected at least partly even without an emitted laser beam, for example by virtue of corresponding sensors being provided which can ascertain the exact position and/or deflection and/or displacement and/or orientation of the control element even without being impinged on by a laser beam.

Optionally, the laser beam is emitted during the functional test of the control element with such a power which is below a power threshold for endangerment and/or processing of an eye. In this case, the power threshold for the processing of the eye is that threshold of the laser energy below which the material or tissue is not changed in regard to the respective application. In this case, the power threshold for the endangerment of the eye is a safety threshold of the laser energy below which no injury to the eye occurs and in particular collateral damage also does not occur at other parts of the eye that are not subjected to the treatment, such as the lens and/or the retina, for instance. The limitation of the power to one of these power thresholds, typically to the power threshold for the endangerment of the eye, allows that the functional check of the control element can at least partly also make use of the laser beam, where application of the laser beam to a patient's eye and/or an object to be processed is not harmful owing to the power below the power threshold. In particular, this affords the advantage that the laser beam can be used during the functional check of the control element in order to detect a provided reference object characterizing the variable parameter.

The variable parameter can optionally characterize a variable element of the laser processing system, such as, for instance, a patient docking unit and in particular a contact glass, a part of the optical system which is subjected to changes, or a laser scanner and the control thereof, which can be subject to drift. Optionally, the variable parameter characterizes a property of the laser processing system and in particular a property of an exchangeable contact glass of the laser processing system. This can be in particular a geometric property of the contact glass. The variable parameter can be variable for instance owing to contact-glass-dependent deviations that occur in the context of production-dictated manufacturing tolerances, for instance, wherein the deviations can nevertheless be manifested in such a way that it appears advisable to take them into account in order to achieve the desired precision during the laser treatment or laser processing. In this regard, the variable parameters of a contact glass can concern for example the thickness and/or the diameter and/or the centration, i.e. the lateral offset relative to the optical axis, and/or the shape, in particular the radius of curvature, and/or other geometric variations of the contact glass or of parts thereof. By ascertaining the variable parameter and determining the influence on the intended carrying out of the laser processing, it is thus possible to reduce or even completely avoid inaccuracies and a reduction of the precision owing to the variable parameter. As reference object, in this case, use can be made of variable manifestations of components of the laser processing system or of the eye per se, or else markings and/or marker elements from which stored information can be read out, such as a barcode or a color marker, for instance. As reference object that is represented by the variable manifestation itself, in this case, use can be made of the contact glass surfaces (beset by deviations between individual contact glasses), in particular. For this purpose, the laser beam or the focus during the test of the laser scanner can be guided in such a way that the laser beam along the scanning path intersects the contact glass surface and that part of the laser beam which is reflected and/or scattered in the process is detected by a reference object sensor and can be received and evaluated by the control unit. The contact glass surface is an optical interface that serves as a reference surface for the patient's eye which is docked to the contact glass surface. In the docked state, the eye assumes the shape of this interface. Therefore, accurate knowledge of the location of this interface in relation to the laser focus position may be of importance for accurate processing of the cornea or other parts of the eye. The assignment of the signals detected from the reference object and the associated scanner positions or positions of the laser beam or of the focus then make it possible to ascertain the geometric properties of the contact glass and thus of the variable parameter. By way of example, for this purpose, it is possible to use a method described in the laid-open application WO 2008/040436 A1. In this case, the scanning pattern along which the laser beam is moved during the process of scanning the contact glass can comprise or consist of a spiral scanning trajectory. By way of example, the scanning trajectory can be designed to be similar or identical to a focus trajectory for a flap incision. Alternatively or additionally, a scan can be performed below the vertex of the spherical interface. In this case, a plane of the real focus positions can intersect the spherical interface in a circle. In other words, a confocal signal arises in the form of a circle, the center point of which corresponds to the vertex point of the interface and the diameter of which indicates the height of the vertex by way of a spherical shape given a known radius of curvature of the interface.

Optionally, the contact glass can have one or more markings which serve as reference object and contain information about the contact glass, such as about the type, shape and/or spatial arrangement, for instance. By way of example, the information can reveal details about a contact glass type, an angular orientation, a shape-describing parameter and/or a serial number, for example by means of a barcode. In this case, the markings can provide information about the variable parameter in particular by way of their spatial positioning and/or orientation in and/or on the contact glass. Alternatively or additionally, it is possible to form one or more reference objects which provide information by way of other properties rather than by way of their positioning and/or orientation. For example, it is possible to form such reference objects as markers whose properties can be detected by the reference object sensor upon detection by means of the laser beam. For example, the markers can provide a luminescence signal having a predetermined wavelength, such that corresponding information can be extracted on the basis of the wavelength or color of said signal. For example, the contact glass size can be indicated by a corresponding luminescence color code.

In this case, the control signals for the laser scanner can be designed such that they correspond exactly to those of a treatment for the x- and y-scanners. The z-scanner is controlled slightly differently than a treatment, such that the contact glass surface is reliably intersected by the focus trajectory. The laser radiation is active during the system test, but is attenuated optionally to a safe level (laser class 1). Further parameters of the laser radiation can be regulated and/or monitored during the system test just like during the actual treatment (e.g., pulse picking). Optionally, a confocal optical unit with a photodiode as sensor serves as reference object sensor for the scanning process. In this case, a part of the incident laser beam firstly can be reflected from the contact glass surface back into the incident laser beam and can be split off from the main path via a polarizing beam splitter. On the basis of the detected signal, the variable parameter can then be ascertained and used for the optimization of the control signals for the laser scanner in order to increase the accuracy of the treatment.

Optionally, the variable parameter concerns a property of an eye to be treated by means of the laser processing system, in particular a variable spatial position of the eye relative to the laser processing system. In this case, a surface in the eye that reflects and/or scatters a part of the laser beam optionally serves as reference object. By way of example, the iris and/or the retina and/or the cornea or parts thereof can constitute such a surface. Therefore, e.g., the orientation and/or positioning of the eye that is docked to the laser processing system can be ascertained during the functional check of the control element.

Optionally, the variable parameter concerns a variable property of a measuring unit of the scanning device, in particular of a signal conversion unit, wherein at least one part of an optical element in the beam path of the laser processing system with previously known geometry serves as reference object. In this case, for example, the known surface of the optical element serving as reference object, for instance the surface of a lens in the beam path of the laser beam, can be scanned by the laser beam or optionally by the focus of the laser beam and the shape of the surface determined by the measuring unit can be compared with the known, actual shape. From a possible deviation owing to the variable parameter, it is then possible to derive information for an optimization of control signals for the control element, for instance for the laser scanner or the scanning device, in order to at least partly compensate for the deviation. A corresponding optimization method can also be applied to other variable elements if the latter have an influence on the control of the laser scanner.

Optionally, the method furthermore comprises checking at least one further component of the laser processing system from the following list: a shutter unit, a pulse picker unit, an attenuator unit. Therefore, one or more of these further tests, too, can be carried out at least partly simultaneously with the further tests and/or calibrations, and the total duration of a system test can be shortened further in this way.

Optionally, the method furthermore comprises checking the laser source, which can be designed as a pulsed laser source, such as a femtosecond laser, for instance, in particular with regard to at least one of the following parameters: pulse energy, peak intensity, pulse frequency, and pulse duration. Therefore, checking the laser source, too, can be carried out at least partly simultaneously with tests and/or calibrations of the laser processing system, and the total duration of a system test can be shortened further in this way.

Optionally, the method furthermore comprises checking one or more safety devices of the laser processing system. This can optionally be carried out temporally after ascertaining the variable parameter but at least partly simultaneously with the functional test of the control element. For this purpose, optionally, a shutter can be positioned in the beam path of the laser beam, such that emergence of the laser beam can be avoided. The functionality of the shutter can be checked in this way. Optionally, the elapsed time between the activation command for triggering the shutter and the complete blocking of the laser beam can be ascertained and compared with a reference value. For example, a photodiode can be used as sensor, said photodiode being arranged behind the shutter, for example. Alternatively or additionally, the shutter can be at least partly designed as a mirror, such that it directs the laser beam onto a photodiode in the closed state. Alternatively or additionally, the photodiode can be embodied as a nonlinear sensor in order in addition to be able to ascertain the peak intensity of the laser pulses.

Optionally, the results of a target-actual comparison of the scanner positions that are ascertained during the system test are compared with predefined tolerance conditions. In this case, compliance with the predefined tolerances may be required for enabling the laser processing system for a treatment and/or processing. Optionally, the properties of the variable element that are ascertained during the system test are also compared with predefined tolerance conditions. In this case, too, compliance with the predefined tolerances may be required for enabling the laser processing system for a treatment and/or processing.

The properties of the variable element that are ascertained during the system test are optionally used to adapt the scanner control signals that are to be generated for a subsequent laser treatment to the ascertained properties (e.g. adaptation of the scanning pattern to the position and/or shape of the contact glass). The scanner movements during the system test optionally completely cover the treatment range that is to be expected or is possible for the scanner. The scanner movements during the system test optionally contain at least parts of the possible scanning range which are representative of scanner movements which typically actually occur during a treatment. Alternatively or additionally, the scanner movements during the system test contain parts of the possible scanning range which are representative of movements for which the greatest probability of the occurrence of a malfunction is expected during a treatment.

Optionally, even further sensors in the laser processing system can be involved in the system test. In this regard, in accordance with exemplary embodiments, it is possible to carry out the system test while the laser optical unit is pivoted out from the treatment position. Depending on the exemplary embodiment, this can lead to a transformation (e.g. rotation) of the function which links the contact glass coordinate system with the scanner control signals. If the location of the contact glass front surface is then ascertained during the system test, for example, in order that the scanner control signals for the subsequent treatment are adapted thereto, the effect of the pivoting-out has to be taken into account. A corresponding sensor that measures the pivoting-out can be provided for this purpose.

Furthermore, optionally, one or more properties of one or more variable elements can be measured In the case of a contact glass detection, various contact glass surface parameters such as location, shape, boundary, surface properties and/or contamination can be ascertained, for example.

Moreover, an iterative ascertainment of the properties of the variable element, i.e. of the variable parameter, is optionally possible. In this regard, the ascertainment of variable parameters concerning the contact glass surface can include the following parts:

Part 1: Measurement of the approximate location of the contact glass at three points.

Part 2: A more accurate measurement of the shape along a plurality of lines is carried out on the basis of the results from Part 1.

The light which, at a contact glass surface, is reflected and/or scattered to a contact glass detection unit serving as reference object sensor, on the way to the detection unit, for example, can traverse the same path as the incident laser beam or follow a different path. By way of example, for detecting the scattered and/or reflected portion of the laser beam, it is possible to use a confocal detection, as described in the laid-open publication WO 2009/146906 A2, for instance. In the former case, for example, a beam splitter can be used to separate the incident light from the reflected light. This beam splitter can optionally in turn have a constant splitting ratio or utilize polarization effects. Furthermore, this beam splitter (and possibly associated elements such as waveplates) can optionally be removed from the beam path after the system test. Instead of a laser beam attenuation during the test, optionally, a beam trap behind the last relevant optical surface can also prevent emergence of intensive laser radiation.

Optionally, even further parameters concerning the contact glass can be detected. Known properties are often used as location reference in this case. The detection time or test duration can be kept short as a result. Given a known surface shape of the contact glass surface, for example three measurement points in space can be sufficient in order to determine the exact location of the contact glass surface.

The method and the control unit are optionally also applicable to excimer lasers that do not generate a defined laser focus. In this case, for example, it is possible to check the correct fit of a patient interface and/or the size thereof, and/or the scaling of a measuring unit of the laser scanner. In this case, accordingly, the conditions concerning the laser focus are then omitted and are generally replaced by the (non-focused) laser beam. The detection of the position of the reference object is then possible primarily laterally.

The laser source used during the system test need not necessarily be identical with that used for the treatment, although this is the case in some exemplary embodiments.

In this case, the exemplary embodiment of the detection unit for the reference object sensor can vary in different exemplary embodiments. By way of example, the reference object sensor can have a photodiode and/or a camera. In the case of a photodiode, the latter can be an optional part of a confocal observation for the contact glass detection. A camera could additionally detect scattered light from markings introduced by laser treatment in a contact glass.

The features and exemplary embodiments specified above and explained below should not only be considered to be disclosed in the respective explicitly mentioned combinations in this case, but are also comprised by the disclosure in other technically advantageous combinations and embodiments.

BRIEF DESCRIPTION OF THE DRAWINGS

Further details and advantages of the disclosure will now be explained in more detail on the basis of the following exemplary embodiments with reference being made to the figures, in which.

DESCRIPTION OF EXEMPLARY EMBODIMENTS

The same or similar elements in the various exemplary embodiments are denoted by the same reference signs in the following figures for reasons of simplicity.

Figure 1:
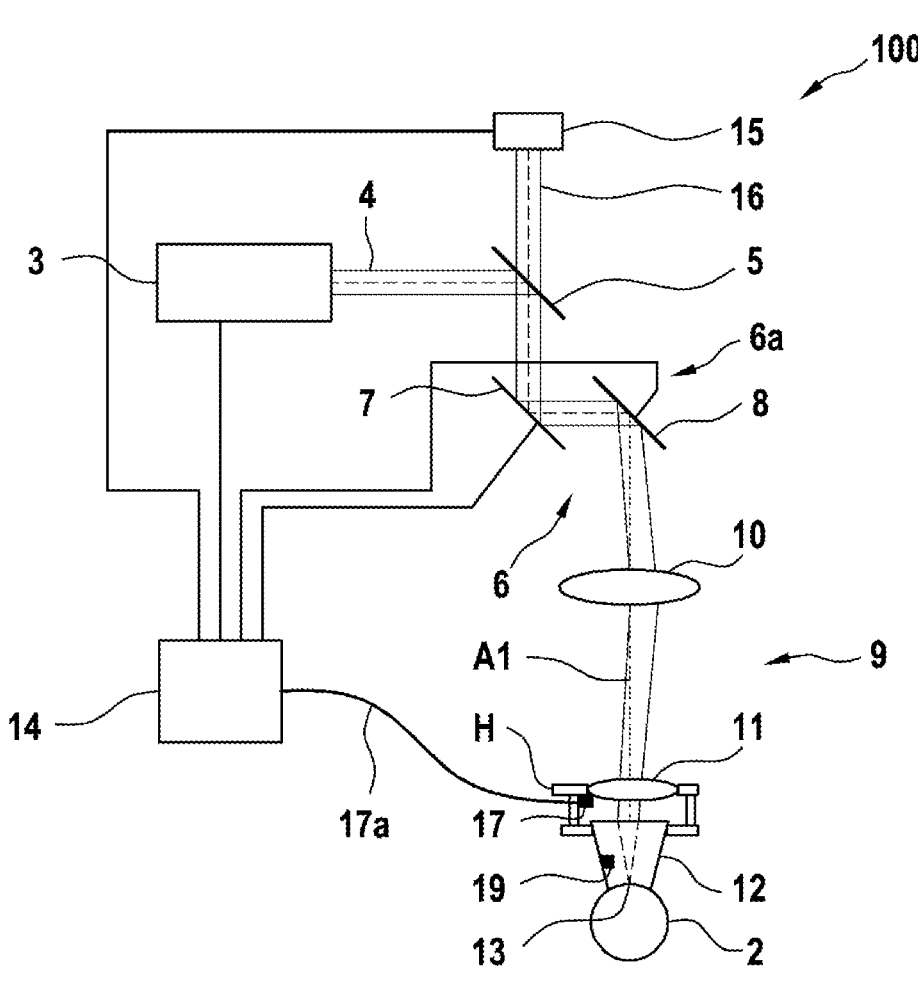
FIG. 1 shows a laser processing system 100 in accordance with one exemplary embodiment' and FIG. 2 shows an elucidation of the interaction of a plurality of components for a system test in accordance with one exemplary embodiment.

FIG. 1 shows a schematic illustration of a laser processing system 100 in accordance with one exemplary embodiment, which system is designed as an apparatus for refractive surgery on an eye. The laser processing system 100 is accordingly designed as treatment equipment and serves to carry out, using a laser beam, a refractive error correction on an eye 2 of a patient by means of a method for refractive surgery. To this end, the apparatus 100 comprises a laser or laser source 3, which emits pulsed laser radiation. In this case, the pulse duration is in the femtosecond range, for example, and the laser radiation acts on the cornea of the eye 2 in order to separate the lenticule from the surrounding cornea within the cornea.

The laser beam or treatment beam 4 emitted by the laser source 3 along an optical axis A1 is in this case incident on a beam splitter 5, which guides the laser beam 4 to a control element 6 designed as a scanning device 6a. In accordance with the exemplary embodiment shown, the scanning device 6a has two scanning mirrors 7 and 8 which are rotatable about mutually orthogonal axes such that the scanning device 6a deflects the treatment beam 4 in two dimensions. An adjustable projection optical unit 9 focuses the treatment beam 4 onto or into the eye 2. In this case, the projection optical unit 9 has two lens elements 10 and 11.

A contact glass 12 is disposed downstream of the lens element 11 and is connected securely to the lens element 11 and hence to the laser processing system 100 by way of a holder H. The contact glass 12 rests on the cornea of the eye 2. The optical combination of contact glass 12 and the other optical components of the laser processing system 100 causes the treatment beam 4 to be focused at a focus 13 located within the cornea of the eye 2.

The apparatus 100 furthermore comprises a control unit 14, which is configured, in particular, to control the scanning device 6a, the laser 3 and the projection optical unit 9. Moreover, the control unit 14 is configured to monitor the functionality of the apparatus and, for this purpose, to carry out a system test for checking the functionality of the laser processing system 100. For this purpose, the control unit 14 can subject elements of the laser processing system 100 to a test and/or a calibration. In this case, the control unit 14 can cause the elements of the laser processing system 100 to carry out predetermined processes, which are then monitored by way of suitable sensors and/or detectors. The measurement data used in this case by the sensors and/or detectors are then fed to the control unit 14 again and can be used by the latter for checking the functionality and for the further control of the laser processing system 100.

Even though the exemplary embodiment shown illustrates only one control unit, a plurality of control units which carry out the specified tasks and/or other tasks may also be provided in accordance with other exemplary embodiments.

The laser processing system 100 additionally has a reference object sensor 17, which serves for ascertaining a variable parameter concerning the contact glass 12 in accordance with the exemplary embodiment shown. In this case, the reference object sensor 17 is arranged in the region between the contact glass 12 and the lens element 11 and is configured to detect parts of the incident laser beam that are reflected and/or scattered by the contact glass and to communicate the measurement results via a communication line 17a to the control unit 14 for further evaluation. In accordance with other exemplary embodiments, however, the reference object sensor can also be arranged elsewhere. By way of example, the detector 15 can also serve as a confocal reference object sensor. As reference object 19, in this case, for example, use can be made of a marking within the contact glass which backscatters and/or reflects a part of the incident laser beam such that, on the basis of the backscattered and/or reflected part of the laser beam, information concerning the variable parameter can be ascertained, such as, for instance, regarding geometric dimensions and/or orientations of the contact glass 12. Alternatively or additionally, the reference object 19, if detected by the laser beam, can emit a luminescence signal which is detectable by the same reference object sensor 17, and further information, such as regarding the size of the contact glass, for instance, is obtainable therefrom by the control unit 14. This can be done for example by way of the evaluation of the wavelength or color of the luminescence signal. In this case, the luminescence can be based on fluorescence and/or phosphorescence.

Further, the control unit 14 reads a detector 15 of the laser processing system 100, which detector detects radiation backscattered and/or reflected by the cornea, which radiation passes through the contact glass 12 and passes the beam splitter 5 as reflection radiation 16. To this end, there can be confocal imaging of the backscattered reflection radiation 16 on the detector 15. This detector, too, in accordance with an exemplary embodiment, can serve as reference object sensor and can ascertain a variable parameter concerning the eye 2. For example, by means of the detector, information about the positioning and/or orientation of the eye 2 can be ascertained as a (further) variable parameter and can be forwarded to the control unit 14. The reference object 19 can be formed by a property of the cornea or from the interior of the eye 2.

Figure 2:
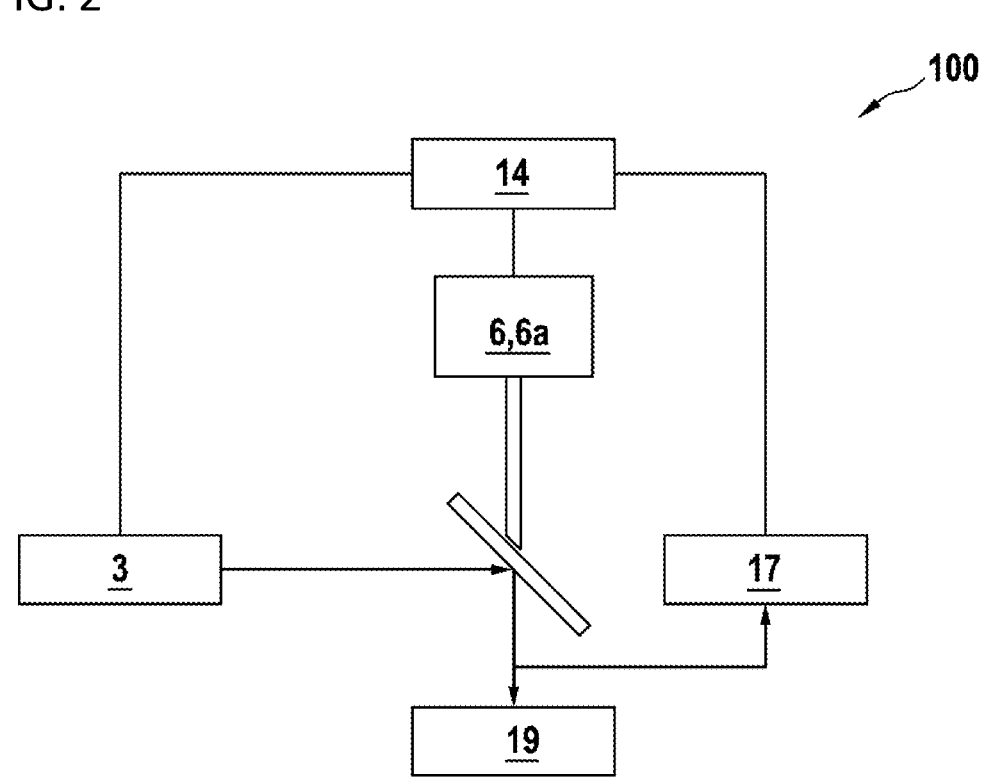

A method for carrying out a system test of the laser processing system 100 in accordance with one exemplary embodiment is explained below with reference to FIG. 2, which shows a schematic illustration of the interaction of the laser source 3, the scanning device 6a, the reference object 19, the reference object sensor 17 and the control unit 14.

In this case, for example, a variable parameter characterizing the contact glass 12 is intended to be ascertained. The variable parameter that is intended to be ascertained in the context of the system test is in this case the exact location of the front side of the cornea, which is influenced by the exact geometric dimensions of the contact glass 12. Owing to the deviations between the different eyes and the resultant changes in the variable parameter, an accurate ascertainment of the variable parameter is advantageous for achieving a high level of precision. Particularly with the use of non-applanation-type contact glasses, the differences between different eyes can greatly influence the achievable level of precision. Even with applanation-type contact glasses, however, small deviations between otherwise identical contact glasses 12 may occur owing to manufacturing tolerances, and ought to be taken into account in order to achieve a high level of precision.

In order to keep the duration of the system test short, in accordance with the exemplary embodiment explained, the functional test of the scanning device 6 serving as a control element, and ascertaining the variable parameter (exact location of the front side of the cornea; determined by contact glass) are carried out at least partly simultaneously. In this case, the functional test of the scanning device 6a comprises moving mirrors along a scanning pattern into those positions which are required for the planned treatment, and optionally into even further positions. For this purpose, the mirrors of the scanning device 6a can be provided with suitable angle sensors, for example. The measurement data of the angle sensors are communicated to the control unit. Simultaneously, at the points in time at which the scanning device is set in the context of the functional check along the scanning path in such a way that a laser beam passing through is incident on the reference object 19 situated in the contact glass, the laser beam is released so that the reference object 19 is detected by the laser beam. It should be noted here that this takes place during the ongoing functional check of the scanning device and both processes are thus carried out simultaneously. In this case, the reference object 19 detected by the laser beam sends a signal to the reference object sensor 17. This signal can include for example a reflected and/or scattered part of the laser beam and/or a luminescence signal excited by the laser beam. The measurement data detected by the reference object sensor 17 are then communicated to the control unit 14 and evaluated by the latter.

Consequently, the functionality includes firstly the control of the laser source 3 and the scanning device 6a for carrying out the system test, and also the at least partly simultaneous reception of measurement data which are detected by the sensors of the scanning device (e.g. angle sensors of the mirrors) during the functional test and are communicated to the control unit, and also the reception of the measurement data communicated by the reference object sensor 17. The control unit 14 should therefore be configured in such a way that it copes with simultaneously performing this plurality of tasks. In particular, the control unit 14 is to be configured with a corresponding processor power and also with corresponding main memory capacity. The control unit 14 can then carry out a target-actual comparison on the basis of the received and evaluated measurement data and can compare the result with predetermined tolerance values. If the result of the system test then ascertained by the control unit 14 indicates a fault-free function of the laser processing system 100, the control unit can enable the laser processing system for the treatment. If the result of the system test does not indicate sufficient functionality of the laser processing system, the control unit 14 can prevent the treatment from being carried out and/or can output a corresponding warning indication to the user.

LIST OF REFERENCE SIGNS

2 Eye
3 Laser
4 Laser beam
5 Beam splitter
6 Control element
6a Scanning device
7 Scanning mirror
8 Scanning mirror
9 Projection optical unit
10 Lens element
11 Lens element
12 Contact glass
13 Focus
14 Control unit
15 Detector
16 Reflection radiation
17 Reference object sensor
17a Communication line
19 Reference object
100 Laser processing system
A1 Optical axis

The invention claimed is:

1. A method for carrying out a system test of a laser processing system, the method comprising:
    carrying out a functional test of a control element of the laser processing system; and
    ascertaining a variable parameter and determining an influence of the ascertained variable parameter on an intended carrying out of laser processing with the laser processing system, wherein the variable parameter concerns a property of an eye to be treated with the laser processing system or a contact glass surface which serves as an optical interface and as a reference surface for the eye to be treated when docked to the contact glass surface, wherein a surface of the eye which reflects and/or scatters a part of the laser beam or the contact glass surface which reflects and/or scatters a part of the laser beam serves as a reference object;

wherein carrying out the functional test of the control element and ascertaining the variable parameter overlap one another at least partly in time, wherein the control element is a scanning device for beam deflection, and the functional test of the control element is a test of the scanning device with at least one control element sensor, wherein the test of the scanning device includes controlling the scanning device such that the scanning device is set in accordance with a scanning pattern for guiding a laser beam along a predetermined scanning path, wherein a respective setting of the scanning device for deflecting the laser beam with the scanning device is ascertainable with the at least one control element sensor, and wherein the scanning pattern is configured such that the laser beam in the region of the scanning path at least partly detects the reference object characterizing the variable parameter.

2. The method as claimed in claim 1, wherein the scanning pattern is configured such that the resulting scanning path comprises at least some focus positions which are provided for predetermined laser processing by the laser processing system.

3. The method as claimed in claim 2, wherein the variable parameter is ascertainable based on a signal resulting therefrom.

4. The method as claimed in claim 3, wherein the signal resulting from the detection of the reference object by the laser beam comprises a reflected portion of the laser beam and/or a scattered portion of the laser beam and/or an emission signal excited by the laser beam, and wherein the signal is detectable by a reference object sensor.

5. The method as claimed in claim 3, wherein the laser beam is emitted only at locations of the predetermined scanning path through the laser processing system at which the laser beam at least partly detects the reference object.

6. The method as claimed in claim 1, wherein the laser beam is emitted during the functional test of the control element with a power which is below a power threshold for endangerment and/or processing of an eye.

7. The method as claimed in claim 1, wherein the variable parameter concerns a property of the laser processing system.

8. The method as claimed in claim 3, wherein the variable parameter concerns a variable property of a measuring unit of the scanning device.

9. The method as claimed in claim 1, further comprising:
checking at least one further component of the laser processing system from the following list:
a shutter unit, a pulse picker unit, or an attenuator unit.

10. The method as claimed in claim 1, further comprising:
checking the laser source with regard to at least one parameter of the laser source.

11. A control unit for a laser processing system, wherein the control unit is configured, in a context of a system test of the laser processing system to:
carry out a functional test of the control element of the laser processing system; and ascertain a variable parameter and to ascertain an influence of the variable parameter on intended carrying out of laser processing by means of the laser processing system, wherein the variable parameter concerns a property of an eye to be treated with the laser processing system or a contact glass surface which serves as an optical interface and as a reference surface for the eye to be treated when docked to the contact glass surface, wherein a surface of the eye which reflects and/or scatters a part of the laser beam or the contact glass surface which reflects and/or scatters a part of the laser beam serves as a reference object, and carry out the functional test of the control element and the ascertaining of the variable parameter in a manner overlapping one another at least partly in time and to receive and/or to evaluate resultant measurement data and/or measurement results at least partly simultaneously, wherein the control element is a scanning device for beam deflection, and the functional test of the control element is a test of the scanning device with at least one control element sensor, wherein the test of the scanning device includes controlling the scanning device such that the scanning device is set in accordance with a scanning pattern for guiding a laser beam along a predetermined scanning path, wherein a respective setting of the scanning device for deflecting the laser beam with the scanning device is ascertainable with the at least one control element sensor, and wherein the scanning pattern is configured such that the laser beam in the region of the scanning path at least partly detects the reference object characterizing the variable parameter.

12. A laser processing system comprising the control unit as claimed in claim 11.

13. The laser processing system as claimed in claim 12, wherein the laser processing system is an apparatus for refractive surgery on an eye.

14. The method as claimed in claim 1, wherein the variable parameter is a variable spatial position of the eye relative to the laser processing system.

15. The method as claimed in claim 8, wherein the variable parameter concerns a signal conversion unit, and wherein at least one part of an optical element in the beam path of the laser processing system with previously known geometry serves as the reference object.

16. The method as claimed in claim 9, wherein the laser source is a pulsed laser source and wherein the pulsed laser source is checked with regard to at least one of the following parameters: pulse energy, peak intensity, pulse frequency, and pulse duration.

17. The method as claimed in claim 1, wherein the iris and/or the retina and/or the cornea or parts thereof can constitute the surface in the eye which serves as the reference object.

18. The method as claimed in claim 1, wherein the contact glass surface serves as the reference object and the reference surface for the eye by forcing the surface of the eye to assume the shape of the contact glass surface when the eye is docked to the optical interface provided by the contact glass surface.

* * * * *